United States Patent [19]
Mah

[11] Patent Number: 5,651,373
[45] Date of Patent: Jul. 29, 1997

[54] EXTENSION DEVICE, ASSEMBLY THEREOF, HEATER FOR USE THEREWITH AND METHOD

[75] Inventor: Kathleen M. Mah, Palo Alto, Calif.

[73] Assignee: Cardiometrics, Inc., Mountain View, Calif.

[21] Appl. No.: 399,940

[22] Filed: Mar. 6, 1995

Related U.S. Application Data

[63] Continuation of Ser. No. 126,522, Sep. 24, 1993, abandoned.

[51] Int. Cl.⁶ .................................................. A61B 5/00
[52] U.S. Cl. ........................................ 128/772; 604/905
[58] Field of Search ...................... 128/772; 604/905; 403/265, 268, 269, 292, 293; 228/132, 133, 904

[56] References Cited

U.S. PATENT DOCUMENTS

| | | | |
|---|---|---|---|
| Re. 34,466 | 12/1993 | Taylor et al. | 128/772 X |
| 934,711 | 9/1909 | Chapman | 403/272 X |
| 1,732,825 | 10/1929 | Wilson, Sr. | 403/272 X |
| 2,490,359 | 12/1949 | Johnson | 403/269 X |
| 2,703,724 | 3/1955 | Der Yuen et al. | 403/265 |
| 3,633,266 | 1/1972 | Taylor | 228/132 X |
| 3,756,635 | 9/1973 | Beers | 403/292 X |
| 4,033,668 | 7/1977 | Presby | 228/904 X |
| 4,507,119 | 3/1985 | Spencer | 604/905 X |
| 4,827,941 | 5/1989 | Taylor et al. | 128/772 X |
| 4,922,923 | 5/1990 | Gambale et al. | 128/772 |
| 5,188,621 | 2/1993 | Samson | 128/772 X |

*Primary Examiner*—Sam Rimell
*Attorney, Agent, or Firm*—Flehr, Hohbach, Test, Albritton & Herbert

[57] ABSTRACT

Flexible elongate extension device for use with a flexible elongate member having proximal and distal extremities, comprising a flexible elongate extension member having proximal and distal extremities. A sleeve is secured to the distal extremity. The sleeve is sized to receive the proximal extremity of the flexible elongate member. A thermoplastic adhesive is disposed in the sleeve and has a lumen therein sized so it is adapted to receive the proximal extremity of the flexible elongate member.

24 Claims, 1 Drawing Sheet

EXTENSION DEVICE, ASSEMBLY THEREOF, HEATER FOR USE THEREWITH AND METHOD

This is a continuation of application Ser. No. 08/126,522 filed Sep. 24, 1993, now abandoned.

This invention relates to a flexible elongate extension device, assembly thereof, heater for use therewith and method which is particularly useful in medical applications.

Guidewire extension capabilities have heretofore been provided by the use of extension wires which are coupled to the guidewire by taking a conventional guidewire having a length in the range of 175 centimeters and providing it with an exchange length with the use of an extension wire for a total length, as for example 300 centimeters. Such extension wires are typically used in angioplasty and other interventional procedures. Exchange capabilities typically have been provided by a mechanical connection in the form of a friction fit between the proximal extremity of the guidewire and the distal extremity of the extension wire. Mechanical connections of this type have disadvantages in that they may accidentally decouple. Such mechanical connections have also been found to be unsuitable for very small diameter guidewires which have small core wires with electrical capabilities associated therewith. There is therefore a need for a new connection capability for use with guidewires overcoming those disadvantages.

In general, it is an object of the present invention to provide a flexible elongate extension device, assembly thereof, heater for use therewith and method which is particularly useful in medical procedures.

Another object of the invention is to provide a device, assembly thereof and heater for use therewith and a method which makes use of a thermoplastic adhesive.

Another object of the invention is to provide a device, assembly thereof and heater for use therewith and a method which is particularly adapted for use with small guidewires.

Another object of the invention is to provide a device, assembly thereof and heater for use therewith and a method which is particularly adapted for use with guidewires and extension wires where such extension wires can be readily attached and detached.

Another object of the invention is to provide a device, assembly thereof and heater for use therewith and a method in which a coupling or joint is provided which has increased strength.

Another object of the invention is to provide a device, assembly thereof and method which substantially reduces the possibility of damage to the guidewire and extension wire while making connections between the same.

Another object of the invention is to provide a heater which can be readily used for making couplings for attaching extension wire to the guidewire and for detaching the extension wire from the guidewire.

Another object of the invention is to provide a heater of the above character which facilitates making the connections between the extension wire and the guidewire.

Additional features and objects of the invention will appear from the following description in which the preferred embodiments are set forth in conjunction with the drawings.

In general, the flexible elongate extension device of the present invention is for use with a flexible elongate member having proximal and distal extremities. The flexible elongate extension device has proximal and distal extremities. A sleeve is secured to the distal extremity. The sleeve is sized to receive the proximal extremity of the flexible elongate member. A thermoplastic adhesive is disposed in the sleeve.

Figure 1:
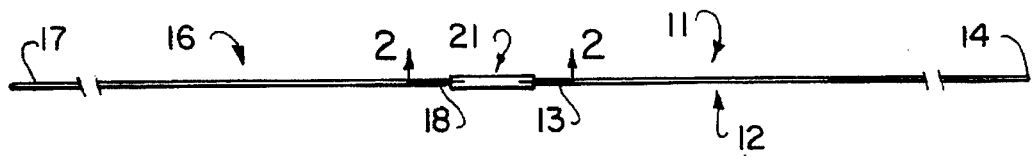
FIG. 1 is a side elevational view of a guidewire with an extension wire coupled thereto in accordance with the present invention.
Figure 2:
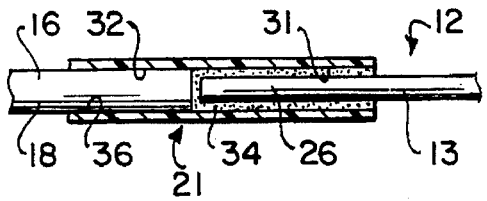
FIG. 2 is a greatly enlarged cross-sectional view taken along the line 2—2 of FIG. 1 showing the coupling or joint shown in FIG. 1.

More specifically, the assembly 11 incorporating the present invention consists of a flexible elongate member 12 typically in the form of a guidewire which has proximal and distal extremities 13 and 14 and a flexible elongate extension member 16 which typically is called an extension wire which is provided with proximal and distal extremities 17 and 18 and a sleeve or a coupling 21 that is provided for coupling the distal extremity 18 of the flexible elongate extension member 16 to the proximal extremity 13 of the flexible elongate member 12. The flexible elongate member 12 can be in the form of a conventional guidewire with the exception that the core wire 26 typically provided therein can have a proximal extremity which is straight such as shown in FIG. 2 rather than being crimped or having other mechanical type friction inducing means carried thereby, as for example screw threads.

The guidewire 12 can be of the type described in U.S. Pat. No. 4,961,433 which is provided with a transducer (not shown) on the distal extremity which is connected by connectors extending through the flexible elongate member or guidewire 12 to conductive elements, as for example slip rings carried by the proximal extremity of the guidewire. The flexible elongate member 12 can have any suitable length, as for example any conventional length for guidewires ranging from 150–190 centimeters and can have a diameter ranging from 0.038 inches and less. The core wire 26 in such a construction can range in diameter from 0.004 inches to 0.028 inches and typically for small wires can have a diameter of approximately 0.0065 inches.

The flexible elongate extension member in the form of an extension wire 16 typically can be of a conventional construction formed of stainless steel and can have a length corresponding to the length of the guidewire so that the length of the guidewire when coupled to the extension wire has a length of approximately 300 centimeters or greater. The extension wire 16 can have a suitable diameter, as for example from 0.008 inches to 0.038 inches.

The sleeve or coupling 21 can have a suitable length ranging from 0.5 centimeters to 2 centimeters and typically can have a length of 1 centimeter. Also it is formed of a suitable material such as stainless steel and it should have a wall thickness ranging from 0.001 inches to 0.004 inches. The sleeve or coupling 21 is sized so that it can receive the distal extremity of the flexible elongate extension member 16 and the proximal extremity of the flexible elongate member 12. Thus, by way of example, the sleeve 21 can have an outside diameter ranging from 0.010 inches to 0.038 inches so that it can accommodate the flexible elongate member 12 and the flexible elongate extension member 16.

The sleeve 21 as well as the guidewire 12 and the extension wire 16 generally would have the same outside diameter.

The sleeve or coupling 21 is provided with the first bore 31 which is sized to receive the proximal extremity 13 of the flexible elongate member 12 and a bore 32 which is sized to receive the distal extremity of the flexible elongate extension member 16. A first means 34 is provided for forming a connection in the bore 31 between the proximal extremity 13 of the flexible elongate member 12 and the sleeve 21 and a second means 36 is provided in the bore 32 for forming a connection between the distal extremity 18 of the flexible elongate extension member 16 and the sleeve 21 whereby the flexible elongate extension member 16 is coupled to the flexible elongate member 12 so that the flexible elongate extension member 16 forms an extension of the flexible elongate member 12. At least one of the first and second means 34 and 36 is formed of a thermoplastic adhesive.

Figure 3:
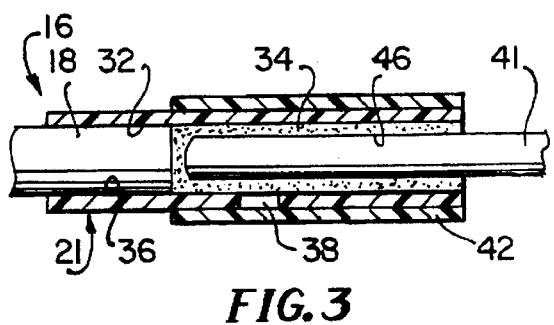
FIG. 3 is an enlarged view showing the method for making the coupling shown in FIG. 2.

As shown in FIGS. 2 and 3, the first means 34 is in the form of the thermoplastic adhesive whereas the second means 36 is in the form of a connection between the distal extremity 18 of the extension member 16 and the sleeve 21 and is of a suitable type such as a tight friction or crimp fit or a solder or adhesive bond. The thermoplastic adhesive must be of a type which permits repeated attachment and detachment so that the flexible extension member 16 and the flexible elongate member 12 can be repeatedly joined together and separated from each other. In other words, the adhesive should not be thermo-setting. One thermoplastic adhesive found to be particularly suitable is identified as 111-14 flexible hot melt adhesive supplied by Creative Materials Incorporated, 141 Middlesex Road, Tyngsboro, Mass., 01879. It has been found that this particular adhesive is very accommodating to flexing and creasing and can be rebonded a number of times by simply repeatedly applying heat and pressure. The initially uncured adhesive is viscous at room temperatures and can be introduced into the bore 31 merely by dipping the coupling into adhesive and permitting the adhesive to wick up into the bore by capillary action. If necessary, this capillary action can be enhanced by providing one or more circumferentially spaced-apart slits 38. Alternatively, the adhesive 34 can be introduced in the bore 31 by placing a vacuum on the proximal end of the bore 31.

It is desirable that the adhesive 34 merely line or partially fill the bore 31. In order to ensure that this takes place, a mandrel 41 having a diameter which is approximate to the diameter of the proximal extremity of the flexible elongate member 12 is utilized and inserted therein immediately after the adhesive has been wicked up into the bore 31. With the mandrel 41 still in place, the adhesive 34, can be dried at room temperature followed by curing for a period ranging from 5 to 10 minutes at 110° C. However, satisfactory curing can be obtained at temperatures ranging from 50° C. to 110° C. To ensure that the adhesive 34 will remain within the bore 31 and will not bleed out through the slits 38, a small piece of tubing 42 is placed over the exterior of the sleeve 21 overlying the slits 38 and is left in place during curing.

After curing has been completed, the mandrel 41 can be removed so that there remains a lumen 46 which is adapted to receive the proximal extremity 13 of the flexible elongate member 12.

Although it has been described that the sleeve or coupling 21 is carried by the distal extremity 18 of the flexible elongate extension member 16, it should be appreciated that if desired, the sleeve or coupling 21 can be carried by the proximal extremity 13 of the flexible elongate member 12 for the first means 34 and that the adhesive be utilized for the second means 36 for connecting the sleeve to the distal extremity 18 of the flexible elongate extension member 16. However, normally it is desirable to not have the proximal extremity of the flexible elongate member 12 be encumbered by such a sleeve particularly when the flexible elongate member 12 is utilized to provide electrical information from the distal extremity 14.

A heater 51 is provided for softening the thermoplastic adhesive utilized in the sleeve or coupling 21 and consists of a case 52 having a lower or a base part 53 and an upper or cover part 54. The case 52 can be formed of a suitable material such as plastic and is provided with a top wall 56 overlying a compartment 57. The top wall 56 is provided with a groove 61 extending transversely of the same and has a cross section in the form of a semi-circle having a diameter accommodating the largest guidewire or extension wire to be utilized therewith. By way of example, assuming that 0.014 inch guidewires are to be utilized, the groove 61 can have a diameter of 0.020 inches.

Figure 4:
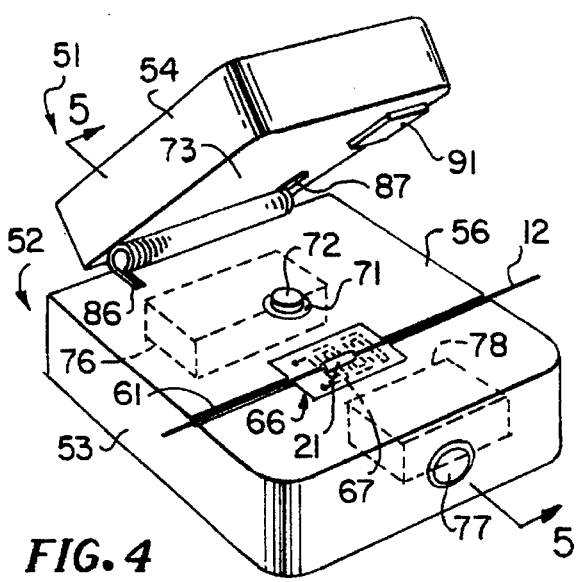
FIG. 4 is an isometric view of a heater incorporating the present invention for use in making the assembly shown in FIG. 2.

A heating assembly 66 is embedded in the top wall 56 and underlies a portion of the groove 61 centrally thereof as shown in FIG. 4 and consists of a heating element 67 having a conventional serpentine pattern which is embedded between upper and lower layers 68 of a suitable insulating plastic 68. The heating element 67 can cover a suitable area, as for example an area of approximately 0.75 inch by 0.5 inch. A push button type switch 71 is mounted in the top wall 56 and is provided with a push button 72 which is adapted to be engaged by the bottom wall 73 when the top cover 54 is moved in engagement with the base 53 as hereinafter described. Thus, as shown in the circuit in FIG. 6, the push button switch 71 is utilized for connecting the heating assembly 66 to a battery 76 of a conventional type, as for example a 9 volt lithium battery mounted within the compartment 57. A lamp 77 is mounted on the lower base 53 and is positioned in a suitable manner, as for example so it can be seen from the front side when the cover 54 is in the closed position to indicate when the switch 71 is energized. A timer 78 is also provided in the compartment 57 and is provided for deactivating the push button 71 after a predetermined interval of time has elapsed which is a period of time that is sufficient to cause softening of the thermoplastic adhesive to permit attachment or detachment to be made as hereinafter described.

Means is provided for permitting swinging movement of the cover 54 with respect to the base 53 for movement between open and closed positions and consists of a conventional piano type hinge 81. A coil spring 84 is mounted on the hinge 81 and is provided with ends 86 and 87 with one end 86 engaging the top wall 56 of the base 53 and the other end 87 engaging the bottom wall 73 of the cover 54. Thus, it can be seen that the coil spring 84 serves to yieldably urge the cover 54 towards an open position with respect to the base 53. Alternatively, a molded living hinge (not shown) of the same plastic as the base 53 and the cover 54 and formed integral therewith can be provided to permit swinging movement of cover 54 with respect to the base 53. Means (not shown) is provided for preventing the cover from opening beyond a predetermined angle with respect to the base 53 as for example beyond an angle of more than 75°.

A friction pad 91 formed of a suitable material such as foam rubber is mounted on the bottom wall 73 by a suitable means such as an adhesive and is positioned off to one side of the wall 73 so that when the cover 54 is moved to a closed position, the pad 91 overlies the groove 61 and is adapted to engage a flexible elongate element or guidewire disposed therein to frictionally retain the same within the groove 61 to inhibit longitudinal movement of the flexible elongate member in the groove 61.

Operation and use of the assembly 11 and the heater 51 in performing the method of the present invention may now be briefly described as follows. Let it be assumed that a conventional angioplasty procedure is being performed and that the guidewire, as for example a 0.014 inch guidewire has been positioned in an arterial vessel of the patient, as for example in a vessel of the heart and that it is desired to exchange a balloon dilatation catheter of a certain size for a larger size balloon dilatation catheter. In such a procedure, typically it is desired to have the guidewire remain in place and to utilize an extension wire. Thus, by way of example let it be assumed a guidewire of the type described in U.S. Pat. No. 4,961,433 has been utilized which provides blood flow velocity measurements. The proximal extremity of such a guidewire can be separated from the instrumentation and a flexible elongate extension member 16, as for example an extension wire 16 which has been provided with the coupling or sleeve 21 of the present invention can be utilized for making an extension. After the rotary connector which is utilized with such a guidewire has been disconnected, the distal extremity of the flexible elongate extension member 16 with the sleeve or coupling thereon is positioned in the left hand side of the groove 61 so that the sleeve 21 is centrally disposed over the heating assembly 66. The physician while holding the distal extremity 18 of the flexible elongate extension member 16 with one hand grasps the proximal extremity 13 of the flexible elongate member or guidewire 12 and positions it on the right hand side of the groove 61 and then slips the proximal extremity into the lumen 46 in the adhesive 34. While holding the assembly in one hand, the cover 54 is swung downwardly to bring the foot 91 into engagement with the flexible elongate member or guidewire 12 to hold the guidewire 12 in place and to ensure that the sleeve 21 overlies the heating assembly 66. The aforementioned procedure can be characterized as a "left-handed" procedure with the patient's head to the right of the physician's. Where applicable a "right-handed" procedure can be utilized with the patient's head to the left of the physician.

At the same time as the cover 54 is moved to a closed position, the push button 72 of the switch 71 is actuated to supply power from the battery 76 to the heating element 67. Because of the very small mass of the sleeve 21 and the adhesive 34 contained therein, the thermoplastic becomes liquid very rapidly, as for example within a period of approximately 10 seconds, causing the adhesive to become viscous and to make contact with the proximal end of the flexible elongate member 12 to adhere thereto. When the allotted time is completed as is determined by the timer 78, the circuit to the heater 67 is opened deenergizing the heater 67 and deenergizing the light 77 to indicate to the physician that the heating cycle has been completed. The physician can then release the cover 54 which will spring under the force of the spring 84 to an open position. The adhesive 34 and the sleeve or coupling 21 is then permitted to cool to room temperature, as for example in approximately 10 seconds to permit the adhesive to solidify and firmly retain the proximal extremity 13 of the flexible elongate member 12 therein. When the cooling has been completed, an extension has been provided for the guidewire permitting the angioplasty catheter to be removed and another angioplasty catheter to be inserted over the extension wire and over the guidewire.

As soon as the second angioplasty catheter is in place, the extension wire 16 can be removed by again placing the joint 21 interconnecting the same to the guidewire 12 into a position overlying the heating assembly 66 with the guidewire 12 and the extension wire 16 disposed in the groove 61. Thereafter, the cover can be closed again to cause heating of the coupling 21 and adhesive therein to cause it to soften permitting the proximal extremity 13 of the guidewire 12 to be removed from the coupling 21. This is accomplished by pulling on the flexible elongate extension member 16 to cause the coupling 21 to separate from the proximal extremity 13 of the flexible elongate member 12. Assuming this decoupling has occurred, the cover 54 can be permitted to spring open and the proximal extremity 13 of the flexible elongate member 12 or guidewire removed and connected into the rotary connector from which it was previously disconnected to permit blood flow velocity measurements to be made.

If it is desired to utilize still another balloon dilatation catheter, the same procedure can be utilized to again connect and disconnect an extension wire 16.

From the foregoing it can be seen that there has been provided a flexible elongate extension device, an assembly thereof and heater for use therewith and a method which is particularly efficacious for repetitively connecting and disconnecting extension wires to small guidewires with a complete and secure extension joint being provided. Uni-axial insertion of the proximal extremity of the guidewire into the sleeve is accomplished followed by heating and cooling of the thermo-setting adhesive contained therein. Disconnection only requires heating of the joint and uni-axial separation of the guidewire from the sleeve. In view of the foregoing, it can be seen that the coupling or joint relies upon the bond strength between an adhesive and metal rather than the interlocking strength between two miniature metal pieces which may be easily deformed. In connection with the foregoing method since uni-axial insertion and removal is utilized, there is a reduced need for manipulation of the guidewires and extension wires thereby minimizing the opportunity for damage of the wires.

Figure 7:
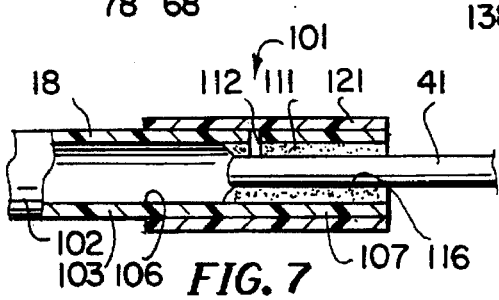
FIG. 7 is a cross-sectional view similar to FIG. 3 incorporating another embodiment of the invention.

Another embodiment of an assembly 101 incorporating the present invention is shown in FIG. 7 and as shown therein consists of a hypotube 102 formed of a suitable material such as stainless steel having a wall 103 forming a lumen 106 extending therethrough. It has a distal extremity 107 which serves as an integral sleeve as shown. An adhesive 111 of the type hereinbefore described is disposed in the distal extremity 107 and is introduced in a suitable manner as hereinbefore described, as for example through radially extending slits 112 provided in the sleeve-like distal extremity 107.

In order to ensure that a lumen 116 remains in the adhesive after it is cured as hereinbefore described, a mandrel 41 of the type hereinbefore described is disposed in the adhesive 111 as shown in FIG. 7. In order to prevent adhesive 111 from bleeding out through the slits 112 during curing, tubing 121, as for example heat shrink tubing can be placed over the distal extremity 107 of the extension wire 102 to close off the slits 38. After the adhesive has cured, the mandrel 41 can be readily removed. Thereafter when desired, a guidewire 12 can be disposed in the lumen 116. Thereafter, the heater 51 hereinbefore described can be utilized for forming a connection between the proximal extremity of the guidewire 12 and the distal extremity 107 of the extension wire 102.

Figure 6:
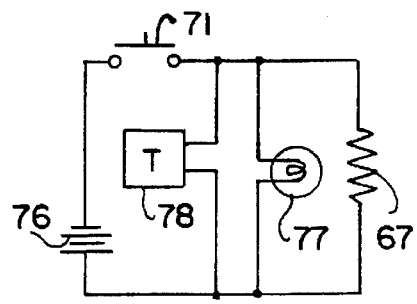
FIG. 6 is a schematic circuit diagram of the electrical circuitry utilized in the heater shown in FIGS. 4 and 5.
Figure 5:
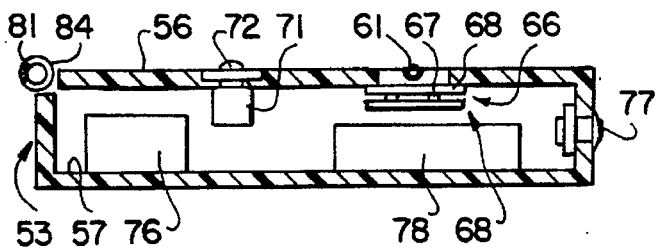
FIG. 5 is a cross-sectional view taken along the line 5—5 of FIG. 4.
Figure 8:
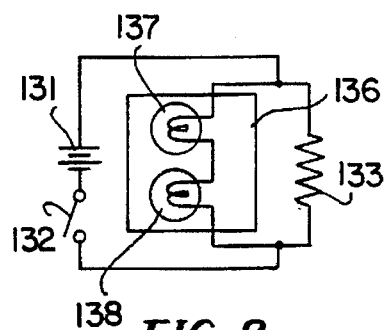
FIG. 8 is a schematic circuit diagram of alternative electrical circuitry to that shown in FIG. 6.

In FIG. 8 there is shown an alternative circuit to the circuit shown in FIG. 6 and as shown therein, it consists of a battery 131 which supplies power through a switch 132 to a heating resistor 133 similar to the heating resistor 67 hereinbefore described. A timing circuit is provided consisting of a timer 136, a red LED 137 and a green LED 138. This circuitry can be mounted in the case or housing in a heater 51 of the type hereinbefore described in an appropriate manner. With the circuitry shown in FIG. 8, the red LED 137 is turned on when energy is supplied to the heater element 133. The timer is arranged so that the green LED 138 is turned on after the desired heating has occurred. Thus, there is no automatic turn off of power to the resistor 133. However, an operator by observing the green light 138 can ascertain when power should be turned off and then operate the switch 132 to shut off the power to the resistor 133.

In view of the foregoing it can be seen that alternative constructions of the present invention can be readily provided.

What is claimed is:

1. A flexible elongate extension device for use in making repetitive connections with a flexible elongate member having proximal and distal extremities comprising a flexible elongate extension member having proximal and distal extremities, a sleeve having first and second portions carried by the distal extremity of the flexible elongate extension member so that the first portion only receives the distal extremity of the flexible elongate extension member, the second portion of said sleeve having a bore sized to receive the proximal extremity of the flexible elongate member so that when the proximal extremity of the flexible elongate member is disposed in the bore, the proximal extremity of the flexible elongate member is in axial alignment with the distal extremity of the flexible elongate extension member and a thermoplastic adhesive disposed in said bore of the second portion of the sleeve which can be repeatedly heated and cooled to make repetitive connections between the sleeve and the proximal extremity of the flexible elongate member.

2. A device as in claim 1 wherein said adhesive is cured and has a lumen therein sized to receive the proximal extremity of the flexible elongate member.

3. A device as in claim 1 wherein said sleeve is formed of a metal and wherein the proximal extremity of the flexible elongate member is formed of metal and wherein said thermoplastic adhesive provides adhesion between metal of the sleeve and the metal of the flexible elongate member.

4. A device as in claim 2 wherein said thermoplastic adhesive is 111-14.

5. A device as in claim 2 wherein said sleeve has an outside diameter ranging from 0.010 to 0.038 inches.

6. A device as in claim 2 wherein said lumen in said thermoplastic adhesive ranges in size from 0.004 inches to 0.028 inches.

7. A device as in claim 1 wherein said sleeve is formed integral with the distal extremity of the extension member.

8. A flexible elongate assembly for making multiple catheter exchanges comprising a flexible elongate member having proximal and distal extremities, a flexible elongate extension member having proximal and distal extremities, a sleeve having a bore sized to receive the proximal extremity of the flexible elongate member and only the distal extremity of the flexible elongate extension member end-to-end without overlapping, first means forming a connection between the distal extremity of the flexible elongate extension member and the sleeve and second means forming a connection between the sleeve and the proximal extremity of the flexible elongate member whereby when the flexible elongate extension member is coupled to the flexible elongate member the flexible elongate extension member forms an extension of the flexible elongate member, at least one of said first and second means including a thermoplastic adhesive capable of being repeatedly heated and cooled for making repetitive connections between the flexible elongate member and the flexible elongate extension member.

9. An assembly as in claim 8 wherein said adhesive is provided with a lumen extending therethrough.

10. An assembly as in claim 8 wherein said sleeve has a diameter ranging from 0.010 inches to 0.038 inches.

11. An assembly as in claim 10 wherein said sleeve is formed of a metal and wherein said proximal extremity of the flexible elongate member and the distal extremity of the flexible elongate extension member are formed of metal and wherein said thermoplastic adhesive forms a metal to metal bond.

12. An assembly as in claim 8 wherein said adhesive is 111-14.

13. A combination of a flexible elongate member having proximal and distal extremities, a flexible elongate extension member having proximal and distal extremities, a coupling having a bore sized to receive the proximal extremity of the flexible elongate member and only the distal extremity of the flexible elongate extension member, the coupling carrying a thermoplastic adhesive and a heater for repeatedly coupling and decoupling the proximal extremity of the flexible elongate member to the distal extremity of the flexible elongate extension member, the heater comprising a unitary base member having a groove therein adapted to receive the proximal extremity of the flexible elongate member and the distal extremity of the flexible elongate extension member, electrical heating means underlying at least a portion of the groove, a cover secured to said base member and movable into a position overlying the electrical heating means and means for supplying energy to the electrical heating means to cause softening of the thermoplastic adhesive carried by the coupling for permitting repeated attachment of the flexible elongate member to the coupling and repeated detachment of the flexible elongate member from the coupling.

14. A heater as in claim 13 together with switch means for energizing and deenergizing the electrical heating means.

15. A heater as in claim 14 wherein said switch is mounted in said base member so that upon moving said cover member to a closed position with respect to the base member the switch means is operated to cause energization of the electrical heating means.

16. A heater as in claim 14 together with timer means for interrupting the heating of the electrical heating means.

17. A heater as in claim 13 together with a visual indicating means for indicating when power is being supplied to the electrical heating means.

18. A heater as in claim 13 together with visual means for indicating when sufficient energy has been supplied to the electrical heating means.

19. In a method for repeatedly joining the proximal extremity of a flexible elongate metal member to the distal extremity of a flexible elongate metal extension member using a coupling having a bore therein having first and second ends and carried thereby and sized to only receive the flexible elongate metal extension member in the first end, the coupling having a thermoplastic adhesive therein and being adapted to receive the proximal extremity of the flexible elongate member in the second end comprising inserting the proximal extremity of the flexible elongate member into the thermoplastic adhesive in the coupling so that the proximal extremity of the flexible elongate member is in an end-to-end relationship with the distal extremity of the flexible elongate member and in axial alignment therewith, heating the coupling and the thermoplastic adhesive therein, permitting the thermoplastic adhesive to cool to form a bond between the flexible elongate member and the flexible elongate extension member so that the flexible elongate extension member serves as an extension to the flexible elongate member and if necessary reheating the coupling and the thermoplastic adhesive therein to permit separation of the flexible elongate member from the flexible elongate extension member and thereafter repeating the aforementioned steps to couple the flexible elongate member to the flexible elongate extension member.

20. A method as in claim 19 together with the step of heating the coupling and the thermoplastic adhesive therein, and separating the flexible elongate extension member from the flexible elongate member.

21. A method as in claim 19 wherein the heating ranges from 55°–100° C.

22. A method as in claim 19 wherein the heating occurs for a period of approximately 5–20 seconds.

23. A method as in claim 22 together with the step of cooling the thermoplastic adhesive for a reasonable period of time after it has been heated.

24. A method for joining the proximal extremity of a guide wire to the distal extremity of an extension wire utilizing a coupling having a thermoplastic adhesive therein and being adapted to receive the proximal extremity of the guide wire and the distal extremity of the extension wire to make it possible to change catheters after a catheter has been placed on the guide wire, comprising placing a balloon catheter on the guidewire inserting the proximal extremity of the guide wire into the thermoplastic adhesive in the coupling, heating the thermoplastic adhesive, permitting the thermoplastic adhesive to cool to form a bond between the proximal extremity of the guide wire and the coupling, removing the balloon catheter from the guide wire while leaving the guide wire in place, introducing another catheter over the extension wire and the guide wire while the guide wire is still in place, heating the thermoplastic adhesive in the coupling and separating the guide wire from the extension wire and if necessary reconnecting the guide wire to the extension wire by inserting the guide wire into the coupling, heating the thermoplastic adhesive and permitting the thermoplastic adhesive to cool.

* * * * *